United States Patent
McBride et al.

(10) Patent No.: US 7,204,992 B2
(45) Date of Patent: Apr. 17, 2007

(54) P153 AND P156 ANTIGENS FOR THE IMMUNODIAGNOSIS OF CANINE AND HUMAN EHRLICHIOSES AND USES THEREOF

(75) Inventors: Jere W. McBride, League City, TX (US); David H. Walker, Galveston, TX (US)

(73) Assignee: Clayton Foundation for Research, Houston, TX (US)

( * ) Notice: Subject to any disclaimer, the term of this patent is extended or adjusted under 35 U.S.C. 154(b) by 43 days.

(21) Appl. No.: 10/701,038

(22) Filed: Nov. 4, 2003

(65) Prior Publication Data

US 2004/0121433 A1    Jun. 24, 2004

Related U.S. Application Data

(60) Provisional application No. 60/423,573, filed on Nov. 4, 2002.

(51) Int. Cl.
*A61K 39/02* (2006.01)
(52) U.S. Cl. .............. 424/234.1; 424/282.1; 530/350; 530/820; 530/825
(58) Field of Classification Search ........... 530/350, 530/820, 825; 424/234.1, 282.1
See application file for complete search history.

(56) References Cited

U.S. PATENT DOCUMENTS

| | | | |
|---|---|---|---|
| 6,355,777 B1 | 3/2002 | Walker et al. | 530/350 |
| 6,436,399 B1 | 8/2002 | Rikihisa et al. | 424/139.1 |
| 2002/0120155 A1 | 8/2002 | Bercovici et al. | 549/287 |
| 2002/0132789 A1 | 9/2002 | Barbet et al. | 514/44 |

FOREIGN PATENT DOCUMENTS

| | | |
|---|---|---|
| WO | WO 98/42846 | 10/1998 |
| WO | WO 01/82862 | 11/2001 |

OTHER PUBLICATIONS

Colman Res. Immunology, Jan. 1994, vol. 145, pp. 33-36.*
McBride et al., "Kinetics of antibody response to *Ehrlichia canis* immunoreactive proteins," *Infection and Immunity*, 71(5):2516-2524, 2003.
McBride et al., "Molecular cloning of the gene for a conserved major immunoreactive 28-kilodalton protein of *Ehrlichia canis*: a potential serodiagnostic antigen," *Clin Diag Lab Immunol*, 6(3):392-399, 1999.
McBride et al., "Immunodiagnosis of *Ehrlichia canis* infection with recombinant proteins," *J. Clin Microbiol*, 39(1):315-322, 2001.
McBride et al., "Identification and functional analysis of an immunoreactive DspA-like thio-disulfide oxidoreductase of *Ehrlichia* spp.," *Infect. Immun*, 70(5):2700-2703, 2002.
Storey et al., "Molecular cloning and sequencing of three granulocytic *Ehrlichia* genes encoding high-molecular-weight immunoreactive proteins," *Infect Immun*, 66(4):1356-1363, 1998.
Unver et al., "Transcriptional analysis of p30 major outer membrane multigene family of *Ehrichia canis* in dogs, ticks, and cell culture at different temperatures," *Infect Immun*, 69(10):6172-6178, 2001.
Yu et al., "Comparison of *Ehrlichia chaffeensis* recombinant proteins for serologic diagnosis of human monocytropic Ehrlichiosis," *Clin Microbio*, 37(8):2568-2575, 1999.
Yu et al., "Molecular cloning and characterization of the 120-kilodalton protein gene of *Ehrlichia canis* and application of the recombinant 120-kilodalton protein for serodiagnosis of canine Ehrlichiosis," *J Clin Microbio*, 38(1):369-374, 2000.
Yu et al., "Cloning and sequenceing of the gene for a 120-kDa immunodominant protein of *Ehrlichia chaffeensis*," *Gene*, 184(2):149-154, 1997.

* cited by examiner

*Primary Examiner*—Robert A. Zeman
(74) *Attorney, Agent, or Firm*—Fulbright & Jaworski LLP

(57) ABSTRACT

Sequences encoding two immunoreactive glycoproteins were cloned from *Ehrlichia canis* (p153 gene) and *Ehrlichia chaffeensis* (p156 gene). These two glycoproteins are species-specific immunoreactive orthologs that are useful as subunit vaccines and for serologic and molecular diagnostics for *E. canis* and *E. chaffeensis*.

5 Claims, 6 Drawing Sheets

```
_110        _120        _130        _140        _150        _160        _170        _180        _190
PRGDVAELQEAVEEDPLYAVPLPKGQRPAPTQVLEEDPSVEEEEIAPPLPPRNNVGEVEPQEDPIYQGIPGHQEEMEEDPYASLDQVSQ
P.GD:.: Q..  .::   .  G    :  .... E  :  E.E::  .  P:..  ....   E      P  .::  P :    S
PSGDIQD-QSQQDQQEQDQQQGAVGGAVGNSPIERERVAAPESEDLYTVIIPKGKRTAAPILERKSPTPEPKVEDDEDLPPTLPPRTFS-
   º20        º30        º40        º50        º60        º70        º80        º90        º100

_200        _210        _220        _230        _240        _250        _260        _270        _280
GAGADGIQENPVPQEAGEELEEDIYQDPADFQGLGQGQQLDQAGYQGPSIGDRQLVNGPYGFNDGSYAMEFD-DVMWEGVRDAVIHDEEID
G.G D::   :::P   :   :  I QD:  .   :G G   .Q .Q  ..:..  G R:::  GPY.F::G    M:F: D. W :VR:AV: .:EI.
GEGYDDV-GVSMPTVSRGIYQPPIVQDSNLYSSIG-GVPQEAQYDAAARAGGPRKFLYGPYTFSNGQEIMDFEFDTPWPDVRNAVLGNKEIK
   º110       º120       º130       º140       º150       º160       º170       º180       º190

_290        _300        _310        _320        _330        _340        _350        _360        _370
PKFLVTDGLMRHICDKIVQSEGNLPEPDLEEIVSILKNDKEGISELINEPVQVDIPNNPVREGRNVMTLLHLAYAYNVDPRIINAIESVE
 ..L.T.G  :R:I D:IV.S.G:L:E  ::EEI:.I:   ...I:E  I:..:D: NNPV.  :: NVMTL:HL.YA..:VDPRI::A:..VE
EEWLTTSGPVRDIADRIVASKGDLSEDQVEEILDIIFMNESEIAEGISNPLHADVDNNPVKGAKNVMTLMHLVYACDVDPRIVKALGEVE
   º200       º210       º220       º230       º240       º250       º260       º270       º280

_380        _390        _400        _410        _420        _430        _440        _450        _460
NSFGESGLDGYNIQDADGNLPLHHAAKNCNGQVLDNCISKTNSNIINIRNFGNQSPLHVMVQNPGCSIGNIQVANECGMDFNLIDHPTGR
N. G:  G   :: YN:   D: :GNLPLHHAAKNC.G:  L.  C::  KT::.::NI:.. NF:NQSPLH:..Q:P:CS: :I:    .  . .:DF.L:D  .G:
NDEGDLGANAYNVLDSEGNLPLHHAAKNCTGDKLKLCMEKTKTDFIDTANFANQSPLHIITQKPDCSVLDIEEFTSRNLDFGLVD-GDGK
   º290       º300       º310       º320       º330       º340       º350       º360       º370

_470        _480        _490        _500        _510        _520        _530        _540        _550
MPIHYAAEAASSEVLSYVIRNTKAESPQASAVNTQDVNGRTPLHCAAISGNSK-GLSVMLLQNGVDCAVRDKNYSTPLHYAVAGNDIKSIK
P:H.A.E  ::  :L. V:  ::L.V: ::K..S   .. VN..D  G.T  H.A.  : N:.  .L  ML  .:G.D .VRL    .:P:H A :.... ::..
NPLHHAVEHLPPVILKGVMDHVKNSSEFQDLVNDPDYFGNTIAHYAVKNKNADLTLFNMLKASGADLNVRNVVGRAPIHVASSNGKANAVS
   º380       º390       º400       º410       º420       º430       º440       º450       º460
```

Fig. 1A

```
   _560        _570        _580        _590        _600        _610        _620        _630        _640
NL--CSVKGRVQGVKSSAA-SLLCEDLQGDTPLHIACKVEGTKAFETVRQSIKKHHGKQVLQELLIREGSGPRLNVSGFGSQSILSGVSGDLY
.L  C:::. Q:V:::::  :  F:  :TL: ::  ::::: .  :       :I:. :::: N:.G  :::: ::: :Y
GLVSCGIDVNSQDVNGDTPLHIAVEGGSMETVLAVLNQRGADVSVQNNDGVTPMLSAAKYGDIGVIKALGSAKPNIKG--EDTVAKSLLMEDY
    º470        º480        º490        º500        º510        º520        º530        º540        º550

_650        _660        _670        _680        _690        _700        _710        _720        _730
GYLNSQNFPTSPVHAAVKANNLQLLNLFLKKSPDI--LRQSSPNGFNPVHMAALFADVKTVKLIIENASGEEVNAQSDSTLTPLHLACIRGD
:::F    V  :::  : ::::::    .K.D:  :R:. ::  :  :::.L  . . L  NA. .  :: ::. :::P:. ::::
KGFTPLHF---VAGGGSRDTFRVVRKNYEKCHDLATIRAALMQDRSGGELVNLGDFESENILGSPNAKFLQHIQSANFGFSPARRGIVSSN
    º560        º570        º580        º590        º600        º610        º620        º630        º640

_740        _750        _760        _770        _780        _790        _800        _810        _820
GSIIKRMVEHESVNVNQTMGPDQNTVLQYAINRGNHSLIKRLL-SHPSIDLNVRNADGKTSAHSAMEKGDLKTVKALCNAGADVNTVDNNG
:::K :::: :  : ::::  . ::..N: :Q A   G:.. :K.L  S   : DLN :::: T: . A  :GD  .V::L  . ::: :.  G
HNVMKDILNFVGDSLHLPSERGYNA-MQVAALFGDKEAVKMLAKSAKPSDLNFKTSATPTPLNLACLRGDNEVVRGLVGQ-HGIDINQRMG
    º650        º660        º670        º680        º690        º700        º710        º720        º730

_830        _840        _850        _860        _870        _880        _890        _900        _910
RSVISSAIYSGQNEKKLVPIVKLLLNSGAKIG-SQEDKNILLQKCINSGYNKLLDLLLEQGERIN-VEGKA-SPLVSAVVSG----NTHAVK
 .. :   Y:  :......:   : K:L :::G:...  ::  . :L:   :::G  K::. :N  ::::: S L  SA:V:G         V:
SDKNTVLHYAISKGDSFL-VQKILAHTGVDVNCENNLGQTPLHLAVEGGDPKIVSSLLKAGAVVNRLDDNGRSVLSSAIVPGRKEKGVLGIVN
    º740        º750        º760        º770        º780        º790        º800        º810        º820

_920        _930
KLVASGGDINQKVSDENSIHYKNSL    (SEQ ID NO: 1)
KL:..G.:DIN  :.....I  :...L
KLLDRGADIN--LDGDHNILFDQCL    (SEQ ID NO: 2)
    º830        º840
```

P153 AND P156 ANTIGENS FOR THE IMMUNODIAGNOSIS OF CANINE AND HUMAN EHRLICHIOSES AND USES THEREOF

CROSS-REFERENCE TO RELATED APPLICATION

This application claims benefit of provisional patent application U.S. Ser. No. 60/423,573, filed Nov. 4, 2002, now abandoned.

FEDERAL FUNDING LEGEND

This invention was produced in part using funds from the Federal government under Grant No. AI31431 from the National Institute of Allergy and Infectious Diseases. Accordingly, the Federal government has certain rights in this invention.

BACKGROUND OF THE INVENTION

1. Field of the Invention

The present invention relates generally to the fields of molecular and immunodiagnostics. More specifically, the present invention relates to species-specific immunoreactive protein orthologs (~200 kDa) from *Ehrlichia canis* and *Ehrlichia chaffeensis* that are useful for species-specific diagnosis of canine ehrlichiosis and human monocytotropic ehrlichiosis.

2. Description of the Related Art

Canine monocytic ehrlichiosis is a potentially fatal tick-borne disease of dogs with worldwide distribution caused primarily by the rickettsial agent, *Ehrlichia canis* (Huxsoll et al., 1970). *E. canis* is an obligately intracellular bacterium that exhibits tropism for monocytes and macrophages (Nyindo et al., 1971), and establishes persistent infections in the vertebrate host (Harrus et al., 1998). The disease is characterized by three stages: the acute stage which lasts 2 to 4 weeks; the subclinical stage, in which dogs can remain persistently infected for years, but do not exhibit clinical signs, followed by the chronic phase, where in many dogs the disease becomes progressively worse due to bone marrow hypoplasia and the prognosis less favorable (Troy et al., 1990).

*Ehrlichia canis* infects and causes ehrlichiosis in animals belonging to the family Canidae. Canine ehrlichiosis consists of an acute and a chronic phase. The acute phase is characterized by fever, serous nasal and ocular discharges, anorexia, depression, and loss of weight. The chronic phase is characterized by severe pancytopenia, epistaxis, hematuria, blood in feces in addition to more severe clinical signs of the acute disease. If treated early during the course of the disease, dogs respond well to doxycycline. However, chronically infected dogs do not respond well to the antibiotic. Therefore, early diagnosis is very important for treating canine ehrlichiosis.

Treating the disease in the acute phase is important for the best prognosis. Hematologic abnormalities such as leukopenia and thrombocytopenia often provide useful evidence of canine ehrlichiosis and are important factors in the initial diagnosis (Troy et al., 1990). However, diagnosis is made difficult because the clinical presentation of canine ehrlichiosis is non-specific.

Diagnosis of canine ehrlichiosis by serologic methods such as the indirect fluorescent-antibody (IFA) test has become the standard method due to its simplicity, reliability and cost effectiveness (Troy et al., 1990). However, shortcomings of the indirect fluorescent-antibody test include the inability to make a species-specific diagnosis due to antigenic cross reactivity with other closely related *Ehrlichia* species that infect dogs (*E. chaffeensis*, *E. ewingii*, *Anaplasma phagocytophilum*, and *A. platys*). Subjective interpretations may also result in false-negative results, or false-positives caused by cross-reactive antigens. Other diagnostic methods such as polymerase chain reaction (PCR) have been developed for specific detection of *E. canis*, and were reported to be more sensitive than cell culture isolation, but this method requires specialized training and expensive equipment (McBride et al., 1996). Isolation of the organism is time consuming, and only a few laboratories have been consistently successful with this method. Furthermore, additional tests characterizing the isolate are required for defining a specific etiology using this method.

Serologically cross-reactive antigens shared between *E. canis* and *E. chaffeensis* have been reported. Some of the major serologically cross-reactive proteins exhibit molecular masses of 28–30-kDa (Chen et al., 1997; Rikihisa et al., 1994), and it is now known that these proteins are encoded by homologous multigene families (Ohashi et al., 1998a, b). There are 22 and 25 homologous, but nonidentical, p28 genes that have been identified and sequenced in *E. chaffeensis* and *E. canis*, respectively. Similar intraspecies and interspecies strain homology was observed between the P28 proteins of *E. canis* and *E. chaffeensis*, explaining the serologic cross reactivity of these proteins (McBride et al., 1999).

A recent report demonstrated that the rP28 protein from *E. chaffeensis* was an insensitive tool in diagnosing cases of human monocytotrophic ehrlichiosis (HME) (Yu et al., 1999a). The underlying reason appears to be the variability of the P28 protein among different strains of *E. chaffeensis* (Yu et al., 1999b). Conversely, the P28 genes identified in *E. canis* are conserved among geographically dispersed strains, and the *E. canis* rP28 has proven to be useful for diagnosis of canine ehrlichiosis (McBride et al., 1999; Ohashi 1998a). Other homologous immunoreactive proteins including the glycoproteins in *E. canis* (gp140) and *E. chaffeensis* (gp120) have been cloned (Yu et al., 1997, 2000). Reactivity of the rgp120 of *E. chaffeensis* has correlated well with the indirect fluorescent-antibody for serodiagnosis of human monocytotropic ehrlichioisis, and preliminary studies with the rgp140 of *E. canis* suggest that it may be a sensitive and reliable immunodiagnostic antigen (Yu et al., 1999a, 2000).

The prior art is deficient in specific antigens for serologic and molecular diagnostics for *E. canis* and *E. chaffeensis* as well as methods for such use. The present invention fulfills this longstanding need and desire in the art.

SUMMARY OF THE INVENTION

A strongly immunoreactive 43 kD protein (p43) of *Ehrlichia canis* has been identified (U.S. Pat. No. 6,355,777). As an immunodiagnostic antigen, the p43 had a 96% accuracy as compared with the indirect fluorescent-antibody test and provided species-specific diagnosis of *E. canis* infections. Further investigation revealed that the *E. canis* p43 represents the N-terminal portion of a protein with a predicted molecular mass of 153 kD, the largest immunoreactive protein described in *Ehrlichia* spp. Analysis of recombinant expressed fragments of the p153 by protein gel electrophoresis demonstrated a larger than predicted molecular mass (~10 to 30%) and presence of carbohydrate glycans on N- and C-terminal fragments, indicating that the p153 is a glycoprotein.

A BLASTn search was performed on the available *E. chaffeensis* genome sequence (95%), and the gene encoding the p153 ortholog was identified in *E. chaffeensis*. The *E. canis* p153 (4263-bp) and *E. chaffeensis* p156 (4389-bp) genes had similar chromosomal locations, downstream of the homologous (~87%) deoxyguanosine-triphosphate triphosphohydrolase genes and homologous (~90%) intergenic sequences preceding the open reading frames. Nucleic acid sequence homology (50%) was observed between the glycoprotein genes, supporting previous findings with regard to genetic divergence of the p43 gene fragment, and the p153 and p156 proteins had amino acid similarity of 32%. A native *E. canis* protein with a molecular mass of 200 kD reacted with antisera produced against the N-terminal region (p43) of the p153, suggesting that the native protein was post-translationally modified. Similarly, a recombinant protein comprising the N-terminal region of *E. chaffeensis* p156 migrated larger than predicted (~200 kD), and carbohydrate was detected on the recombinant protein. A major immunoreactive epitope was identified in this N-terminal fragment. The chromosomal location, amino acid homology, and biophysical properties support the conclusion that the p153 and p156 glycoproteins (designated gp200s) are species-specific immunoreactive orthologs.

Major immunoreactive epitopes has been identified in the N-(P43) and C-terminal regions of the *E. canis* p153 and the N-terminal region of the *E. chaffeensis* p156 ortholog that will be useful for serologic diagnostics and vaccines. Furthermore, genes encoding these proteins are species-specific and will be useful for the development of molecular-based diagnostics.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A and 1B show Lipman-Pearson amino acid alignment of the *E. chaffeensis* p156 (top line) and the *E. canis* p153 (bottom line) protein orthologs. Amino acid identities, conserved (:) and semiconserved (.) substitutions are shown in the center.

DETAILED DESCRIPTION OF THE INVENTION

The *E. canis* p43 gene sequence was previously reported as 1173-bp (U.S. Pat. No. 6,355,777), but further analysis revealed a DNA sequencing error resulting in an artificial termination codon and a truncated gene sequence. Using the primer-adaptor gene walking method, an additional 4.5-kbp sequence downstream of the 2.4-kbp in the original p43 clone was determined. The incomplete p43 gene sequence was completed revealing an open reading frame of 4263-bp, which encoded a protein with a predicted molecular mass of 153 kD (designated p153). Upstream of the p153 gene there is an open reading frame encoding a deoxyguanosine-triphosphate triphosphohydrolase and an intergenic noncoding region preceding the p153 gene that have high nucleic acid homology (87% and 90%, respectively) between *E. canis* and *E. chaffeensis*.

A BLASTn search of the *E. chaffeensis* genome sequence with the 2.4-kbp p43 clone identified a highly homologous nucleic acid sequences. A large open reading frame (4389-bp) approximately equivalent in size to the *E. canis* p153 was found in the same chromosomal location with respect to the upstream homologous coding and intergenic nucleic acid sequences and encoded a protein with a predicted molecular mass of 156 kD (p156). Nucleic acid sequence homology (~50%) was observed between the *E. canis* p153 and the *E. chaffeensis* p156 genes; however, the proteins exhibited an overall amino acid sequence similarity of 32% (FIG. 1).

Figures 2A, 2B:
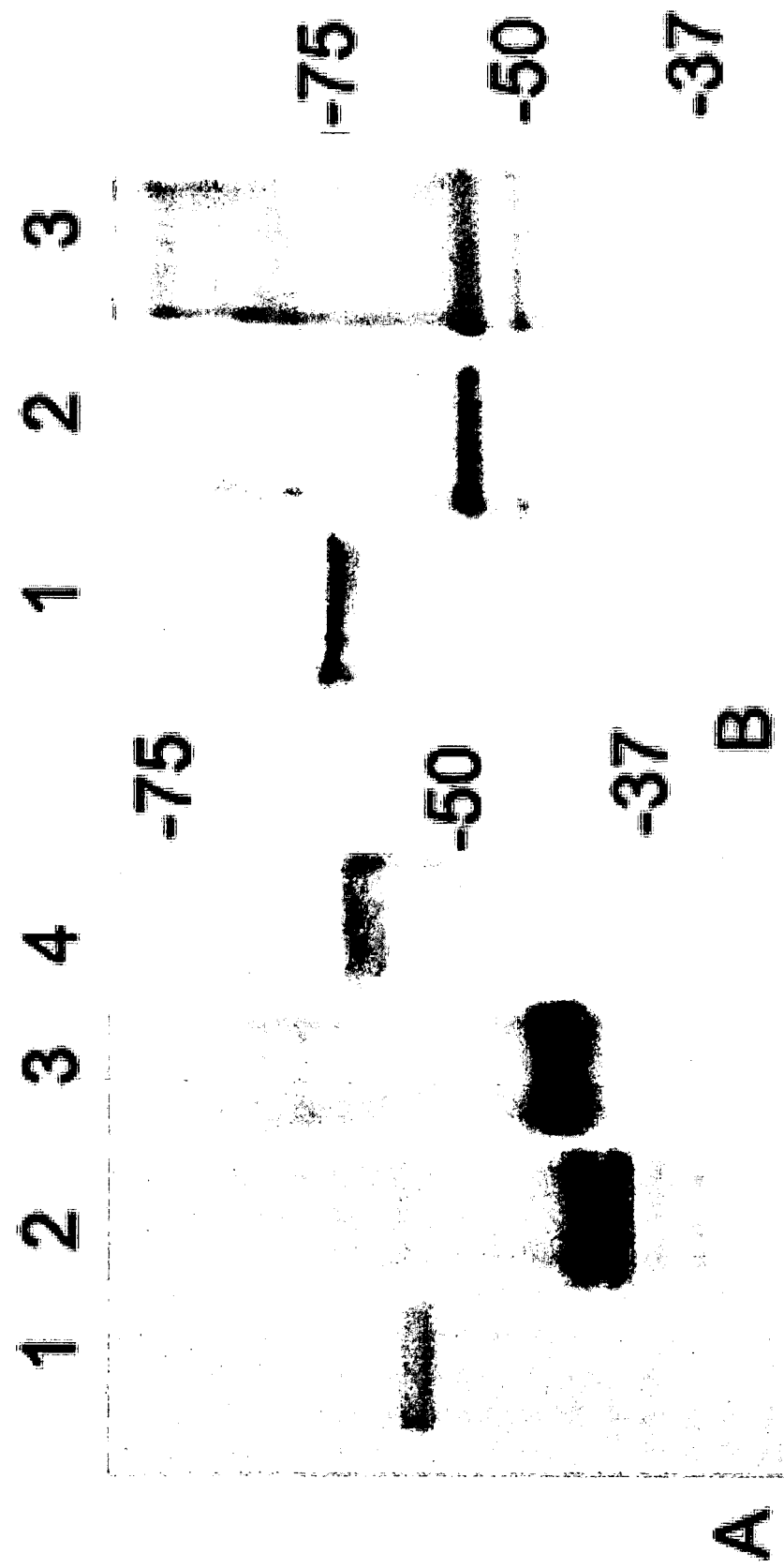
FIGS. 2A and 2B show expression of recombinant protein fragments from the *E. canis* p153 (A) and *E. chaffeensis* (B) and detection with anti-V5 antibody. *E. canis* p153, lane 1, N-terminal fragment (1107-bp, nt-1–1107), lane 2, internal fragment (910-bp, nt-1080–1990), lane 3, internal fragment (1000-bp, nt-1950–2950), and lane 4, C-terminal fragment (1280-bp, nt-2940–4220). *E. chaffeensis* p156, lane 1, N-terminal fragment (1545-bp, nt-125–1675), lane 2, internal fragment (1365-bp, nt-1685–3050), and lane 3, C-terminal (1365-bp, nt-2950–4315).
Figures 3A, 3B:
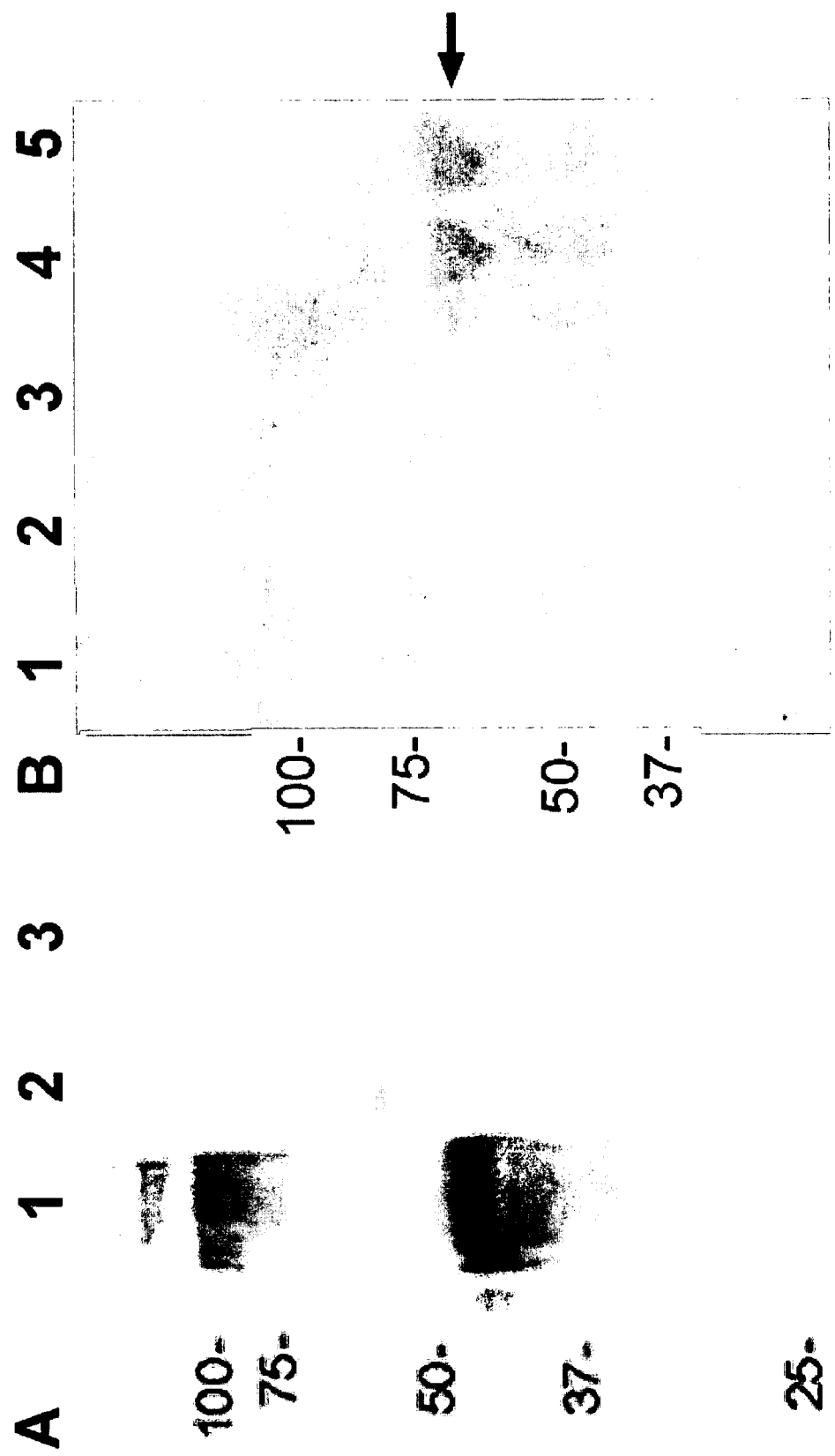
FIG. 3A shows Western immunoblot of *E. canis* p153 recombinant fragments. Lane 1, N-terminal fragment (1107-bp, nt-1–1107), lane 2, internal fragment (910-bp, nt-1080–1990), lane 3, internal fragment (1000-bp, nt-1950–2950), and lane 4, C-terminal fragment (1280-bp, nt-2940–4220).
FIG. 3B shows carbohydrate detection on corresponding purified recombinant fragments of the *E. canis* p153 expressed in *E. coli* using the pRSET expression vector. Glycans attached to the recombinant proteins were oxidized, labeled with biotin and detected with streptavidin-alkaline phosphatase.
Figures 4A, 4B:
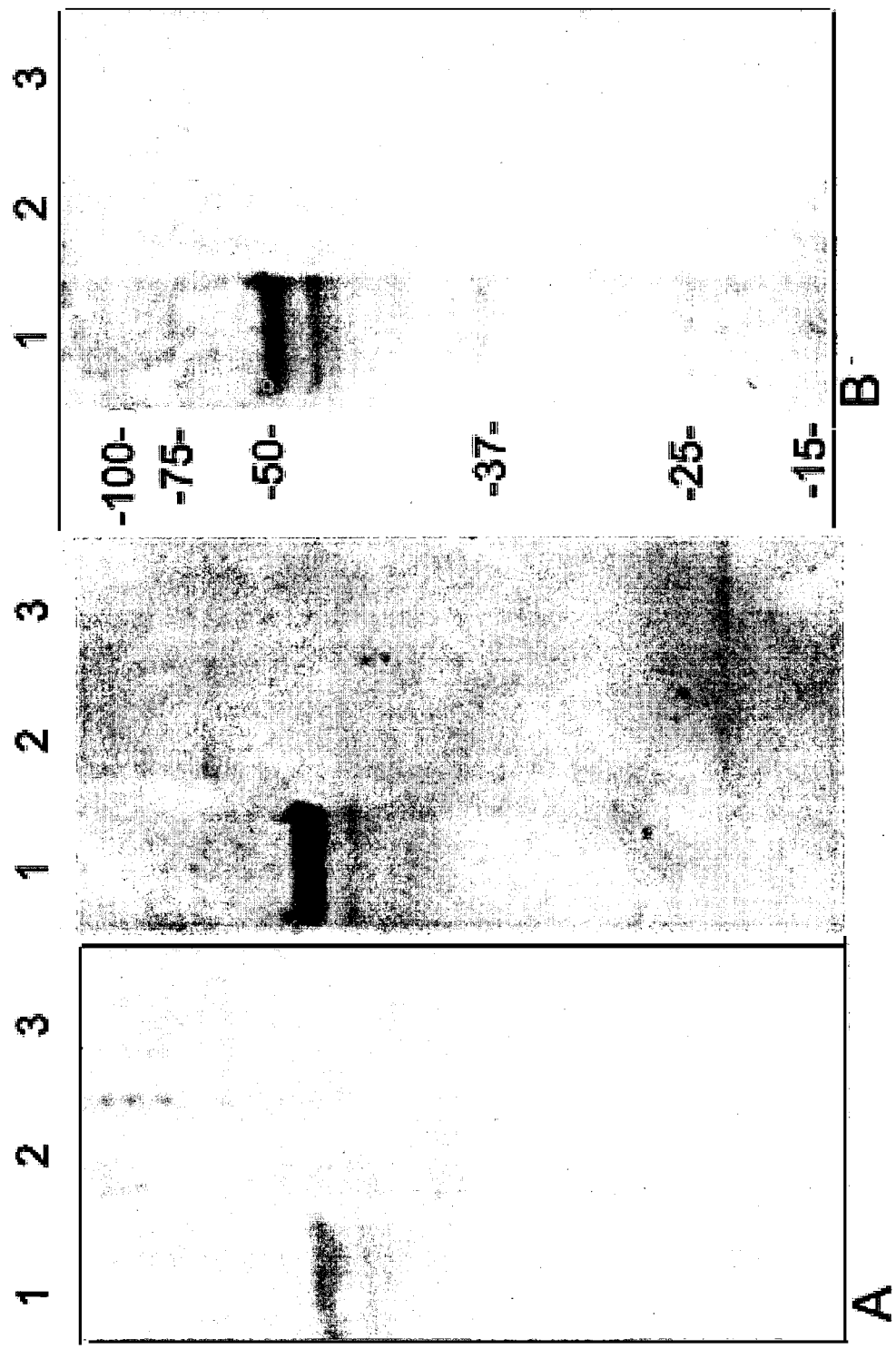
FIG. 4A shows Western blot of the *E. chaffeensis* p156 recombinant fragments (lanes 1–3) with human (left panel) and dog serum (right panel). Lane 1, *E. chaffeensis* p156 N-terminal fragment (1545-bp, nt-125–1675), lane 2, internal fragment (1365-bp, nt-1685–3050), and lane 3, C-terminal (1365-bp, nt-2950–4315). Expressed recombinant proteins represent ~95% of the *E. chaffeensis* p156.
FIG. 4B shows carbohydrate detection of the three corresponding recombinant *E. chaffeensis* p156 proteins (Lanes 1–3).

Gene constructs expressed in *E. coli* representing the *E. chaffeensis* p156 protein (nt-125–1670; nt-1685–3050; nt-2950–4315) and four recombinant fragments of *E. canis* p153 (nt-1–1107 (p43); nt-1080–1990; nt-1950–2950; nt-2940–4220) were expressed in *E. coli* (FIG. 2). The *E. canis* N-terminal (nt 1–1107) and C-terminal (nt-2940–4220) recombinant expressed proteins exhibited strong immunoreactivity (FIG. 3A). However, only the N-terminal fragment (nt-125–1670) of *E. chaffeensis* p156 was immunoreactive (FIG. 4A).

The *E. canis* (nt-1–1107 and nt-2940–4420) and *E. chaffeensis* p156 recombinant proteins fragments (nt-125–1607) migrated larger than predicted by SDS-PAGE indicating that post translational modification of this fragments had occurred. Subsequently, carbohydrate was detected on the *E. canis* p153 and *E. chaffeensis* p156 peptide fragments (FIGS. 3B and 4B).

Figure 5:
FIG. 5 shows Western blot demonstrating the proteins in *E. canis* whole cell lysate with polyclonal antisera from an *E. canis* infected dog (lane 1) and anti-recombinant p43 (gp200) (lane 2) and anti-recombinant gp140 (lane 3) polyclonal rabbit serum.

Anti-p43 antibody reacted with a native protein of approximately 200 kD in *E. canis* whole cell lysates. Furthermore, this 200 kD protein was also recognized by sera from an *E. canis*-infected dog (FIG. 5). A partial gene sequence previously identified as p43 (N-terminal portion of the p153) assigned GenBank accession number AF252298. The amended sequencing encoding p153 was assigned the GenBank accession number AY156950.

The chromosomal location, amino acid homology, and biophysical properties support the conclusion that the p153 and p156 glycoproteins (designated gp200s) are species-specific immunoreactive orthologs. These proteins have potential uses in vaccine development and can be used as sensitive and reliable serodiagnostic antigens for the diagnosis of *Ehrlichia* infections. This is supported by previous findings that showed the immunoreactivity and potential use of the *E. canis* p43 as serodiagnostic antigen (U.S. Pat. No. 6,355,777). Reaction with antibodies against p43 had a 100% correlation with samples having an indirect fluorescent-antibody (IFA) titer>40 and did react with several samples with indirect fluorescent-antibody titers of<40. The weak reactivity of several indirect fluorescent-antibody negative samples with the p43 antibodies suggests that p43 protein may be a more sensitive serodiagnostic antigen. The results presented in the present invention indicate that p43 is part of a larger p153 protein in *E. canis.*

The current invention is directed to isolated polynucleotides encoding *Ehrlichia canis* immunoreactive surface protein p153 and *Ehrlichia chaffeensis* p156 protein. Preferably, the isolated polynucleotides encode the proteins with amino acid sequences shown in SEQ ID No: 1 and 2. Alternatively, the DNA may differ in nucleotide sequence due to the degeneracy of the genetic code.

The instant invention also encompasses vectors comprising these isolated polynucleotides and regulatory elements necessary for expression of the DNA in a cell; isolated and purified p153 and p156 proteins; and antibodies directed against these proteins.

The instant invention is further directed to the use of the p153 and p156 proteins in the preparation of vaccines against canine and human ehrlichioses. In addition, there are provided methods of determining whether a dog or human is infected with an *Ehrlichia* species by determining whether serum from the dog reacts with the p153 or p156 protein. The proteins used may be from recombinant sources, and Western blot analysis may be used to detect the reaction of the serum to the proteins. As reaction with previously isolated *E. canis* p28 protein is also reliable marker of *E. canis* infection, diagnosis may consist of detecting immunoreactivity to the p153 protein, gp140, and the p28 antigens of *Ehrlichia canis.*

The instant invention is also directed to a serodiagnostic kit for determining whether a dog or human is infected with an *Ehrlichia* species. The kit comprises immobilized proteins (p153 or p156) disclosed herein, appropriate dilution buffers for dog serum, anti-dog serum second antibody linked to a reporter molecule, and appropriate reagents for detection of the reporter molecule. Possible methods of immobilizing the antigens include linkage to membranes or microtiter plates. The reporter molecule may be luciferase, horseradish peroxidase, β-galactosidase, or a fluorescent label.

The instant invention is also directed to a PCR amplification method of determining whether a dog has been infected with an *Ehrlichia* species. DNA is extracted from the blood of a potentially infected dog or human and subjected to PCR amplification with oligonucleotide primers specific for the *E. canis* p153 gene or the *E. chaffeensis* p156 gene. The resulting PCR amplification products are separated by size by a method such as gel electrophoresis and detection of an appropriately sized product indicates *Ehrlichia* infection.

The instant invention is also directed to a kit for the PCR detection of the p153 or p156 gene. The kit comprises reagents for DNA extraction from blood, p153 or p156 specific oligonucleotides, and reagents for PCR amplification.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

As used herein, the term "host" is meant to include not only prokaryotes but also eukaryotes such as yeast, plant and animal cells. A recombinant DNA molecule or gene which encodes a protein of the present invention can be used to transform a host using any of the techniques commonly known to those of ordinary skill in the art. Prokaryotic hosts may include *E. coli, S. tymphimurium, Serratia marcescens* and *Bacillus subtilis.* Eukaryotic hosts include yeasts such as *Pichia pastoris,* mammalian cells and insect cells.

In general, expression vectors containing promoter sequences which facilitate efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth. Methods which are well known to those skilled in the art can be used to construct expression vectors containing appropriate transcriptional and translational control signals. See for example, the techniques described in Sambrook et al., 1989, *Molecular Cloning: A Laboratory*

The term "primer" as used herein refers to an oligonucleotide, whether occurring naturally as in a purified restriction digest or produced synthetically, which is capable of acting as a point of initiation of synthesis when placed under conditions in which synthesis of a primer extension product complementary to a nucleic acid strand is induced. The conditions include the presence of nucleotides and an inducing agent such as a DNA polymerase and a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, the oligonucleotide primer typically contains 15–25 or more nucleotides depending on the complexity of the target sequence. Primers with fewer nucleotides may also be used.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

The following examples are given for the purpose of illustrating various embodiments of the invention and are not meant to limit the present invention in any fashion.

EXAMPLE 1

Characterization of *E. canis* p153 and *E. chaffeensis* p156 Proteins

The *E. canis* p43 protein gene was identified from a Lambda Zap II expression library as previously described (McBride et al., 2001; U.S. Pat. No. 6,355,777). The original 2.4-kb clone consisted of an open reading frame (ORF) encoding a deoxyguanosine-triphosphate triphosphohydrolase gene and a downstream 229-bp intergenic space preceding the truncated p43 gene fragment. A primer-adapter PCR method was used to determine the complete sequence of the p43 open reading frame using *E. canis* genomic DNA (Jake, North Carolina strain) as a template. The amplicons were sequenced directly with primers used for amplification or cloned into TOPO/TA for sequence analysis. The *E. chaffeensis* ortholog (p156 gene) was identified by performing a BLASTn search of the *E. chaffeensis* genome sequence with the entire *E. canis* p43 clone (2.4-kb).

The *E. canis* p153 and *E. chaffeensis* p156 genes were divided into large fragments (1 to 1.5-kbp), cloned into pUni/V5-His-TOPO Echo donor vector, and recombined with PBAD Thio-E or pRSET Echo acceptor expression vectors. The recombinant proteins were expressed for 4 h after induction with arabinose or IPTG. Glycan detection on expressed recombinant proteins was performed using an immunoblot kit for glycoprotein detection (Bio-Rad) following the membrane labeling protocol. The *E. chaffeensis* recombinant Dsb protein described previously (McBride et al., 2002) was expressed in *E. coli* and used as an ehrlichial negative control protein for glycoprotein detection studies. *E. canis* whole cell lysates were separated by gel electrophoresis using gradient gels (4–12% Bis-Tris, Novagen) and transferred onto pure nitrocellulose using a semidry transfer unit (Bio-Rad). Immunoblotting was performed as previously described (McBride et al., 2001).

Discussion

The strong immunoreactivity of the clone containing the N-terminal (p43) portion of the *E. canis* p153 led to its initial identification and characterization (McBride et al., 2001). When compared to the results of indirect fluorescent-antibody test for detection of antibodies to *E. canis* in dogs, the p43 exhibited excellent sensitivity and specificity. In addition, the p43 appeared to provide species-specific detection, as anti-recombinant p43 polyclonal antibody did not react with *E. chaffeensis*-infected DH82 cells. The identification of the p153 ortholog in *E. chaffeensis* (p156), which is genetically divergent and has a low degree of amino acid homology, supports previous findings that the p43 protein is a species-specific antigen, and thus would be an excellent species-specific immunodiagnostic antigen. Major linear B cell epitopes are present in the N-(p43) and C-terminal regions of the p153 protein.

The p43 recombinant protein exhibited a larger than predicted molecular mass (~30% or ~10 kD) that was initially unrecognized. Previously reported ehrlichial glycoproteins gp120 and gp140 were 60 to 100% larger than expected. Although the degree of molecular mass shift was much smaller, the p43 protein is a glycoprotein which was confirmed by carbohydrate detection of attached glycans. Consistent with the p43 findings, the expressed *E. chaffeensis* p156 recombinant gene fragments exhibited a larger than expected molecular mass, and carbohydrate was detected on these fragments. Additionally, the C-terminal fragment of the *E. canis* p153 also exhibited larger than predicted molecular mass (~10% or 6 kD).

When the p43 gene was identified, a corresponding native *E. canis* protein from whole cell lysates did not react with anti-p43 antisera. Based on the findings presented here, this discrepancy can be attributed to the fact that the p43 gene represents an incomplete open reading frame, and it does not encode a 43 kD protein. In addition, the large molecular mass of this protein (>150 kD) requires special attention to gel electrophoresis conditions in order to obtain consistent identification of this protein by immunoblot. The 200 kD protein in *E. canis* whole cell lysates was strongly immunoreactive with the anti-p43 polyclonal antibody. The molecular mass of this protein is consistent with the predicted mass of the p153 coupled with some glycans contributing to the increased molecular mass. This finding is also consistent with the molecular mass of the *E. chaffeensis* p156 recombinant fragments representing nearly the entire open reading frame.

Glycoproteins of *Ehrlichia* spp. are some of the first such proteins to be characterized in pathogenic bacteria. The ehrlichial glycoproteins discovered to date are consistently and strongly recognized by antibodies in infected patients and animals. These unique surface-exposed immunoreactive proteins have potential in vaccine development, and these proteins may be important components of subunit vaccines.

The following references were cited herein:

Chen, et al., 1997. Western immunoblotting analysis of the antibody responses of patients with human monocytotropic ehrlichiosis to different strains of *Ehrlichia chaffeensis* and *Ehrlichia canis*. Clin. Diagn. Lab. Immunol. 4:731–735.

Harrus, et al., 1998. Amplification of ehrlichial DNA from dogs 34 months after infection with *Ehrlichia canis*. J. Clin. Microbiol. 36:73–76.

Huxsoll, D. L., P. K. Hildebrandt, and R. M. Nims. 1970. Tropical canine pancytopenia. J. Am. Vet. Med. Assoc. 157:1627–1632.

McBride, et al., 1996. PCR detection of acute *Ehrlichia canis* infection in dogs. J. Vet. Diagn. Invest. 8:441–447.

McBride, et al., 1999. Clin. Diag. Lab. Immunol. 6:392–399.

McBride, et al., 2001. Immunodiagnosis of *Ehrlichia canis* infection with recombinant proteins. J. Clin. Microbiol. 39: 315–322.

McBride, et al., 2002. Identification and functional analysis of an immunoreactive DsbA-like thio-disulfide oxidoreductase of *Ehrlichia* spp. Infect. Immun. 70: 2700–2703.

Nyindo, et al., 1971. Tropical canine pancytopenia: in vitro cultivation of the causative agent—*Ehrlichia canis*. Am. J. Vet. Res. 32:1651–1658.

Ohashi, et al., 1998a. Cloning and characterization of multigenes encoding the immunodominant 30-kilodalton major outer membrane proteins of *Ehrlichia canis* and application of the recombinant protein for serodiagnosis. J. Clin. Microbiol. 36:2671–2680.

Ohashi, et al., 1998b. Immunodominant major outer membrane proteins of *Ehrlichia chaffeensis* are encoded by a polymorphic multigene family. Infect. Immun. 66:132–139.

Rikihisa et al., 1994. Western immunoblot analysis of *Ehrlichia chaffeensis, E. canis,* or *E. ewingii* infections in dogs and humans. J. Clin. Microbiol. 32:2107–2112.

Troy, G. C. and S. D. Forrester. 1990. Canine ehrlichiosis, p. 404–418. In C. E. Green (ed.), Infectious diseases of the dog and cat. W.B. Sauders Co., Philadelphia.

Yu, et al., 1997. Cloning and sequencing of the gene for a 120-kDa immunodominant protein of *Ehrlichia chaffeensis*. Gene 184:149–154.

Yu, et al., 1999a. Comparison of *Ehrlichia chaffeensis* recombinant proteins for serologic diagnosis of human monocytotropic ehrlichiosis. J. Clin. Microbiol. 37:2568–2575.

Yu, et al., 1999b. Genetic diversity of the 28-kilodalton outer membrane protein gene in human isolates of *Ehrlichia chaffeensis*. J. Clin. Microbiol. 37:1137–1143.

Yu, et al., 2000. Molecular cloning and characterization of the 120-kilodalton protein gene of *Ehrlichia canis* and application of the recombinant 120-kilodalton protein for serodiagnosis of canine ehrlichiosis. J. Clin. Microbiol. 38:369–374.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated and purified polypeptide of *Ehrlichia canis* immunoreactive surface protein p153 comprising the amino acid sequence of SEQ ID NO: 2.

2. A composition comprising a p153 polypeptide of claim 1.

3. The isolated and purified polypeptide of claim 1, wherein the protein is immobilized on a surface.

4. The isolated and purified polypeptide of claim 3, wherein the surface is a membrane.

5. The isolated and purified polypeptide of claim 3, wherein the surface is a microtiter plate.

* * * * *

SEQUENCE LISTING

```
<160> NUMBER OF SEQ ID NOS: 2

<210> SEQ ID NO 1
<211> LENGTH: 831
<212> TYPE: PRT
<213> ORGANISM: Ehrlichia canis
<220> FEATURE:
<223> OTHER INFORMATION: immunoreactive surface protein p153

<400> SEQUENCE: 1

Pro Arg Gly Asp Val Ala Glu Leu Gln Glu Ala Val Glu Glu Asp
                5                   10                  15

Pro Leu Tyr Ala Val Pro Leu Pro Lys Gly Gln Arg Pro Ala Pro
                20                  25                  30

Thr Gln Val Leu Glu Glu Asp Pro Ser Val Glu Glu Glu Glu Glu
                35                  40                  45

Ile Ala Pro Pro Leu Pro Pro Arg Asn Asn Val Gly Glu Val Glu
                50                  55                  60

Pro Gln Glu Asp Pro Ile Tyr Gln Gly Ile Pro Gly His Gln Glu
                65                  70                  75

Glu Met Glu Glu Asp Pro Tyr Ala Ser Leu Asp Gln Val Ser Gln
                80                  85                  90

Gly Ala Gly Ala Asp Gly Ile Gln Glu Asn Pro Val Pro Gln Glu
                95                  100                 105

Ala Gly Glu Glu Leu Glu Glu Asp Ile Tyr Gln Asp Pro Ala Asp
                110                 115                 120

Phe Gln Gly Leu Gly Gln Gly Gly Gln Gln Leu Asp Gln Ala Gly
                125                 130                 135

Tyr Gln Gly Pro Ser Ile Gly Asp Arg Gln Leu Val Asn Gly Pro
```

-continued

```
                140                 145                 150
Tyr Gly Phe Asn Asp Gly Ser Tyr Ala Met Glu Phe Asp Asp Val
                    155                 160                 165
Met Trp Glu Gly Val Arg Asp Ala Val Ile His Asp Glu Ile
                170                 175                 180
Asp Pro Lys Phe Leu Val Thr Asp Gly Leu Met Arg His Ile Cys
                    185                 190                 195
Asp Lys Ile Val Gln Ser Glu Gly Asn Leu Pro Glu Pro Asp Leu
                    200                 205                 210
Glu Glu Ile Val Ser Ile Leu Lys Asn Asp Lys Glu Gly Ile Ser
                    215                 220                 225
Glu Leu Ile Asn Glu Pro Val Gln Val Asp Ile Pro Asn Asn Pro
                    230                 235                 240
Val Arg Glu Gly Arg Asn Val Met Thr Leu Leu His Leu Ala Tyr
                    245                 250                 255
Ala Tyr Asn Val Asp Pro Arg Ile Ile Asn Ala Ile Glu Ser Val
                    260                 265                 270
Glu Asn Ser Phe Gly Glu Ser Gly Leu Asp Gly Tyr Asn Ile Gln
                    275                 280                 285
Asp Ala Asp Gly Asn Leu Pro Leu His His Ala Ala Lys Asn Cys
                    290                 295                 300
Asn Gly Gln Val Leu Asp Asn Cys Ile Ser Lys Thr Asn Ser Asn
                    305                 310                 315
Ile Ile Asn Ile Arg Asn Phe Gly Asn Gln Ser Pro Leu His Val
                    320                 325                 330
Met Val Gln Asn Pro Gly Cys Ser Ile Gly Asn Ile Gln Val Ala
                    335                 340                 345
Asn Glu Cys Gly Met Asp Phe Asn Leu Ile Asp His Pro Thr Gly
                    350                 355                 360
Arg Met Pro Ile His Tyr Ala Ala Glu Ala Ser Ser Glu Val
                    365                 370                 375
Leu Ser Tyr Val Ile Arg Asn Thr Lys Ala Glu Ser Pro Gln Ala
                    380                 385                 390
Ser Ala Val Asn Thr Gln Asp Val Asn Gly Arg Thr Pro Leu His
                    395                 400                 405
Cys Ala Ala Ile Ser Gly Asn Ser Lys Gly Leu Ser Val Met Leu
                    410                 415                 420
Leu Gln Asn Gly Val Asp Cys Ala Val Arg Asp Lys Asn Tyr Ser
                    425                 430                 435
Thr Pro Leu His Tyr Ala Val Ala Gly Asn Asp Ile Lys Ser Ile
                    440                 445                 450
Lys Asn Leu Cys Ser Val Lys Gly Arg Val Gln Gly Val Lys Ser
                    455                 460                 465
Ser Ala Ala Ser Leu Leu Cys Glu Asp Leu Gln Gly Asp Thr Pro
                    470                 475                 480
Leu His Ile Ala Cys Lys Val Glu Gly Thr Lys Ala Phe Glu Thr
                    485                 490                 495
Val Arg Gln Ser Ile Lys Lys His His Gly Lys Gln Val Leu Gln
                    500                 505                 510
Glu Leu Leu Ile Arg Glu Gly Ser Gly Pro Arg Leu Asn Val Ser
                    515                 520                 525
Gly Phe Gly Ser Gln Ser Ile Leu Ser Gly Val Ser Gly Asp Leu
                    530                 535                 540
```

```
Tyr Gly Tyr Leu Asn Ser Gln Asn Phe Pro Thr Ser Pro Val His
            545                 550                 555

Ala Ala Val Lys Ala Asn Asn Leu Gln Leu Leu Asn Leu Phe Leu
            560                 565                 570

Lys Lys Ser Pro Asp Ile Leu Arg Gln Ser Ser Pro Asn Gly Phe
            575                 580                 585

Asn Pro Val His Met Ala Ala Leu Phe Ala Asp Val Lys Thr Val
            590                 595                 600

Lys Leu Ile Ile Glu Asn Ala Ser Gly Glu Val Asn Ala Gln
            605                 610                 615

Ser Asp Ser Thr Leu Thr Pro Leu His Leu Ala Cys Ile Arg Gly
            620                 625                 630

Asp Gly Ser Ile Ile Lys Arg Met Val Glu His Glu Ser Val Asn
            635                 640                 645

Val Asn Gln Thr Met Gly Pro Asp Gln Asn Thr Val Leu Gln Tyr
            650                 655                 660

Ala Ile Asn Arg Gly Asn His Ser Leu Ile Lys Arg Leu Leu Ser
            665                 670                 675

His Pro Ser Ile Asp Leu Asn Val Arg Asn Ala Asp Gly Lys Thr
            680                 685                 690

Ser Ala His Ser Ala Met Glu Lys Gly Asp Leu Lys Thr Val Lys
            695                 700                 705

Ala Leu Cys Asn Ala Gly Ala Asp Val Asn Thr Val Asp Asn Asn
            710                 715                 720

Gly Arg Ser Val Ile Ser Ser Ala Ile Tyr Ser Gly Gln Asn Glu
            725                 730                 735

Lys Lys Leu Val Pro Ile Val Lys Leu Leu Leu Asn Ser Gly Ala
            740                 745                 750

Lys Ile Gly Ser Gln Glu Asp Lys Asn Ile Leu Leu Gln Lys Cys
            755                 760                 765

Ile Asn Ser Gly Tyr Asn Lys Leu Leu Asp Leu Leu Leu Glu Gln
            770                 775                 780

Gly Glu Arg Ile Asn Val Glu Gly Lys Ala Ser Pro Leu Val Ser
            785                 790                 795

Ala Val Val Ser Gly Asn Thr His Ala Val Lys Lys Leu Val Ala
            800                 805                 810

Ser Gly Gly Asp Ile Asn Gln Lys Val Ser Asp Glu Asn Ser Ile
            815                 820                 825

His Tyr Lys Asn Ser Leu
            830

<210> SEQ ID NO 2
<211> LENGTH: 831
<212> TYPE: PRT
<213> ORGANISM: Ehrlichia chaffeensis
<220> FEATURE:
<223> OTHER INFORMATION: immunoreactive surface protein p156

<400> SEQUENCE: 2

Pro Ser Gly Asp Ile Gln Asp Gln Ser Gln Gln Asp Gln Gln Glu
            5                   10                  15

Gln Asp Gln Gln Gln Gly Ala Val Gly Gly Ala Val Gly Asn Ser
            20                  25                  30

Pro Ile Glu Arg Glu Arg Val Ala Ala Pro Glu Ser Glu Asp Leu
            35                  40                  45
```

-continued

Tyr Thr Val Ile Ile Pro Lys Gly Lys Arg Thr Ala Ala Pro Ile
            50                  55                  60

Leu Glu Arg Lys Ser Pro Thr Pro Glu Pro Lys Val Glu Asp Asp
            65                  70                  75

Glu Asp Leu Pro Pro Thr Leu Pro Pro Arg Thr Phe Ser Gly Glu
            80                  85                  90

Gly Tyr Asp Asp Val Gly Val Ser Met Pro Thr Val Ser Arg Gly
            95                  100                 105

Ile Tyr Gln Pro Pro Ile Val Gln Asp Ser Asn Leu Tyr Ser Ser
            110                 115                 120

Ile Gly Gly Val Pro Gln Glu Ala Gln Tyr Asp Ala Ala Arg
            125                 130                 135

Ala Gly Gly Pro Arg Lys Phe Leu Tyr Gly Pro Tyr Thr Phe Ser
            140                 145                 150

Asn Gly Gln Glu Ile Met Asp Phe Glu Phe Asp Thr Pro Trp Pro
            155                 160                 165

Asp Val Arg Asn Ala Val Leu Gly Asn Lys Glu Ile Lys Glu Glu
            170                 175                 180

Trp Leu Thr Thr Ser Gly Pro Val Arg Asp Ile Ala Asp Arg Ile
            185                 190                 195

Val Ala Ser Lys Gly Asp Leu Ser Glu Asp Gln Val Glu Glu Ile
            200                 205                 210

Leu Asp Ile Ile Phe Met Asn Glu Ser Glu Ile Ala Glu Gly Ile
            215                 220                 225

Ser Asn Pro Leu His Ala Asp Val Asp Asn Pro Val Lys Gly
            230                 235                 240

Ala Lys Asn Val Met Thr Leu Met His Leu Val Tyr Ala Cys Asp
            245                 250                 255

Val Asp Pro Arg Ile Val Lys Ala Leu Gly Glu Val Glu Asn Asp
            260                 265                 270

Glu Gly Asp Leu Gly Ala Asn Ala Tyr Asn Val Leu Asp Ser Glu
            275                 280                 285

Gly Asn Leu Pro Leu His His Ala Ala Lys Asn Cys Thr Gly Asp
            290                 295                 300

Lys Leu Lys Leu Cys Met Glu Lys Thr Lys Thr Asp Phe Ile Asp
            305                 310                 315

Thr Ala Asn Phe Ala Asn Gln Ser Pro Leu His Ile Ile Thr Gln
            320                 325                 330

Lys Pro Asp Cys Ser Val Leu Asp Ile Glu Glu Phe Thr Ser Arg
            335                 340                 345

Asn Leu Asp Phe Gly Leu Val Asp Gly Asp Gly Lys Asn Pro Leu
            350                 355                 360

His His Ala Val Glu His Leu Pro Pro Val Ile Leu Lys Gly Val
            365                 370                 375

Met Asp His Val Lys Asn Ser Ser Glu Phe Gln Asp Leu Val Asn
            380                 385                 390

Asp Pro Asp Tyr Phe Gly Asn Thr Ile Ala His Tyr Ala Val Lys
            395                 400                 405

Asn Lys Asn Ala Asp Leu Thr Leu Phe Asn Met Leu Lys Ala Ser
            410                 415                 420

Gly Ala Asp Leu Asn Val Arg Asn Val Val Gly Arg Ala Pro Ile
            425                 430                 435

```
His Val Ala Ser Ser Asn Gly Lys Ala Asn Ala Val Ser Gly Leu
                440                 445                 450

Val Ser Cys Gly Ile Asp Val Asn Ser Gln Asp Val Asn Gly Asp
                455                 460                 465

Thr Pro Leu His Ile Ala Val Glu Gly Gly Ser Met Glu Thr Val
                470                 475                 480

Leu Ala Val Leu Asn Gln Arg Gly Ala Asp Val Ser Val Gln Asn
                485                 490                 495

Asn Asp Gly Val Thr Pro Met Leu Ser Ala Ala Lys Tyr Gly Asp
                500                 505                 510

Ile Gly Val Ile Lys Ala Leu Gly Ser Ala Lys Pro Asn Ile Lys
                515                 520                 525

Gly Glu Asp Thr Val Ala Lys Ser Leu Leu Met Glu Asp Tyr Lys
                530                 535                 540

Gly Phe Thr Pro Leu His Phe Val Ala Gly Gly Ser Arg Asp
                545                 550                 555

Thr Phe Arg Val Val Arg Lys Asn Tyr Glu Lys Cys His Asp Leu
                560                 565                 570

Ala Thr Ile Arg Ala Ala Leu Met Gln Asp Arg Ser Gly Gly Glu
                575                 580                 585

Leu Val Asn Leu Gly Asp Phe Glu Ser Glu Asn Ile Leu Gly Ser
                590                 595                 600

Pro Asn Ala Lys Phe Leu Gln His Ile Gln Ser Ala Asn Phe Gly
                605                 610                 615

Phe Ser Pro Ala Arg Arg Gly Ile Val Ser Ser Asn His Asn Val
                620                 625                 630

Met Lys Asp Ile Leu Asn Phe Val Gly Asp Ser Leu His Leu Pro
                635                 640                 645

Ser Glu Arg Gly Tyr Asn Ala Met Gln Val Ala Ala Leu Phe Gly
                650                 655                 660

Asp Lys Glu Ala Val Lys Met Leu Ala Lys Ser Ala Lys Pro Ser
                665                 670                 675

Asp Leu Asn Phe Lys Thr Ser Ala Thr Pro Thr Pro Leu Asn Leu
                680                 685                 690

Ala Cys Leu Arg Gly Asp Asn Glu Val Val Arg Gly Leu Val Gly
                695                 700                 705

Gln His Gly Ile Asp Ile Asn Gln Arg Met Gly Ser Asp Lys Asn
                710                 715                 720

Thr Val Leu His Tyr Ala Ile Ser Lys Gly Asp Ser Phe Leu Val
                725                 730                 735

Gln Lys Ile Leu Ala His Thr Gly Val Asp Val Asn Cys Glu Asn
                740                 745                 750

Asn Leu Gly Gln Thr Pro Leu His Leu Ala Val Glu Gly Gly Asp
                755                 760                 765

Pro Lys Ile Val Ser Ser Leu Leu Lys Ala Gly Ala Val Val Asn
                770                 775                 780

Arg Leu Asp Asp Asn Gly Arg Ser Val Leu Ser Ser Ala Ile Val
                785                 790                 795

Pro Gly Arg Lys Glu Lys Gly Val Leu Gly Ile Val Asn Lys Leu
                800                 805                 810
```

-continued

```
Leu Asp Arg Gly Ala Asp Ile Asn Leu Asp Gly Asp His Asn Ile
                815                 820                 825
Leu Phe Asp Gln Cys Leu
                830
```